(12) United States Patent
Yin et al.

(10) Patent No.: US 7,077,175 B2
(45) Date of Patent: Jul. 18, 2006

(54) PARTICLE PACKING OF MICRODEVICE

(76) Inventors: Hongfeng Yin, 21526 Monrovia St., Cupertino, CA (US) 95014; Kevin P. Killeen, 260 Iris Way, Palo Alto, CA (US) 94303; Reid A. Brennen, 325 Lexington St., San Francisco, CA (US) 94110; Uwe Effelsberg, Zur Ziegelhutte 15, D-76228 Karlsruhe (DE)

( * ) Notice: Subject to any disclaimer, the term of this patent is extended or adjusted under 35 U.S.C. 154(b) by 155 days.

(21) Appl. No.: 10/821,543

(22) Filed: Apr. 9, 2004

(65) Prior Publication Data

US 2005/0224134 A1 Oct. 13, 2005

(51) Int. Cl.
*B65B 1/04* (2006.01)
(52) U.S. Cl. .......................... 141/67; 141/130; 422/99; 422/100
(58) Field of Classification Search ................ 141/130, 141/67, 98; 422/99, 100; 366/108, 208, 366/332, 348, 349, DIG. 3
See application file for complete search history.

(56) References Cited

U.S. PATENT DOCUMENTS 6,581,441 B1   6/2003 Paul
6,610,978 B1*  8/2003 Yin et al. .................... 250/288
6,814,859 B1* 11/2004 Koehler et al. .......... 210/198.2
6,818,184 B1* 11/2004 Fulwyler et al. ............ 422/68.1
6,845,968 B1*  1/2005 Killeen et al. .............. 251/304
6,916,113 B1*  7/2005 Van de Goor et al. ...... 366/108
2002/0142481 A1 10/2002 Andersson et al.
2003/0015682 A1  1/2003 Killeen et al.
2003/0017609 A1  1/2003 Yin et al.

FOREIGN PATENT DOCUMENTS

WO   WO 01/38865    5/2001
WO   WO 01/85341   11/2001
WO   WO 02/075775   9/2002

OTHER PUBLICATIONS

Oleschuk et al. (2000), "Utilization of Beach Based Reagents in Microfluidic Systems," *Micro Total Analysis Systems 2000*, pp. 11-14, van den Berg et al. (Editors), Kluwer Academic Publishers, Netherlands.

* cited by examiner

*Primary Examiner*—Steven O. Douglas

(57) ABSTRACT

Provided are apparatuses and methods for introducing particles into a microdevice conduit. Also provided are microdevices containing a plurality of particles that occupy at least about 25 volume percent of a microconduit. In some instances, particles may controllably form a particle bridge in a bridging zone within a microdevice.

43 Claims, 6 Drawing Sheets

PARTICLE PACKING OF MICRODEVICE

TECHNICAL FIELD

The present invention generally relates to the introduction of particles into a microdevice conduit. More specifically, the invention relates to the application of pressure to a slurry of particles contained in a dispenser to effect transport of the particles into the conduit via slurry flow through a dispensing orifice of the dispenser and an inlet of the microdevice. Optionally, the microdevice conduit may be shaped to control and/or eliminate formation of particle bridges therein.

BACKGROUND

Microfluidics and lab-on-a-chip technologies, also referred to as microdevice technologies, have been proposed for use in the field of analytical and bioanalytical chemistry, particularly in applications that employ fluids that are rare, expensive, and/or available in limited amounts. Such applications include, for example, proteomics, and genomics. The small size of microdevices allows for the analysis of minute quantities of sample. In addition, because microdevices typically have a simple construction, they are in theory inexpensive to manufacture. Furthermore, the small size associated with microdevice may also contribute to increased detection/analytical sensitivity. Such increased sensitivity have been observed in certain nanoflow applications involving liquid chromatography and mass spectrometry.

Microdevices may also be advantageously used to integrate a plurality of functions into a single device. For example, a single microdevice may be adapted carry out a number of different separation techniques, including chromatographic separation techniques that are often preferred for samples containing analyte molecules with low electrophoretic differences, e.g., small drug molecules. Chromatographic separation occurs when a mobile phase carries sample molecules through a chromatography bed (stationary phase) where they interact with the stationary phase surface. The velocity at which a particular sample component travels through a chromatography bed depends on the component's partition between mobile phase and stationary phase.

Ordinary liquid chromatography techniques may be carried out by using a packed column, e.g., a column containing chromatographic separation beads of 1 to 20 μm in diameter. Mechanical or other types of pumps may be employed to generate sufficient pressures to drive a sample through the column. Such pressure-driven, bead-based separation technologies may be employed in conjunction with microfluidic approaches. For example, U.S. Patent Application Publication No. 20030017609 to Yin et al. describes a microdevice that employs pressure-driven flow to effect component separation in a fluid using chromatographic beads. Such pressure driven technologies may be used in conjunction with flow switching structures described in U.S. Patent Application Publication No. 20030015682 to Killeen et al.

Given the dimensional limitations and the surface force effects associated with microdevices, it is not a trivial matter to introduce chromatographic media into a microdevice conduit. Only a few techniques for packing and trapping such media in microdevice conduits are alluded to in the art. In general, these techniques require the use of microdevices having a relatively complex design and/or construction. In turn, specialized equipment may be necessary for manipulating the microdevices and/or loading of the chromatographic media into the microdevices. Furthermore, these techniques generally do not give reproducible results and are not easily adaptable for automation.

For example, International Publication No. WO 01/38865 describes a packing method that employs electrokinetic flow to transfer particles into a chamber within a microfluidic device. The chamber is associated with weir structures that serve to confine the particles therein. However, this method is difficult to implement for at least two reasons. First, electrokinetic flow is practicable only with certain combination of channel surfaces and fluids. Second, weir structures of microfluidic devices require exacting dimensional precision for operability. Such precision is generally difficult to achieve and maintain for microdevices made from flexible polymeric materials such as polyimide.

Weir structures are also described in U.S. Pat. No. 6,581,441 to Paul. Thus, the microdevice loading technology therein suffers from some of the same drawbacks as the technology described above. In addition, the microdevice loading technique described in this patent requires insertion of capillaries into the inlets of the microdevice to be loaded. As discussed in International Publication No. WO 01/85341, the capillaries may be subsequently glued on for permanent attachment of the capillary to the microdevice. Regardless of whether the capillary is permanently attached to the microdevice, the precision needed for such capillary insertion operations are not easily adapted for automation.

To avoid using frit structures, International Publication No. WO 02/075775 and related U.S. Patent Application Publication No. 20020142481 to Andersson et al. describe technologies that use centripedal forces to pack microconduits. To achieve the centripedal forces for microconduit loading, disc shaped microdevices are required. In addition, the microdevices are described as having a specialized microconduit construction to keep loaded particles in place. Thus, it should be evident that while this approach avoids the complexities associated the manufacture of weirs, such complexities are replaced with the manufacturing challenges associated with specialized microconduit designs and geometries required for the application of centripedal forces.

Thus, there is an unrecognized need in the art for improved apparatuses and methods for introducing particles into microdevices. The invention meets this need by employing standardized equipment with minor modifications of such equipment rather than specialized equipment to effect automatic handling and loading of microdevices in a reproducible manner. In addition, the invention is adaptable for use with microdevices of simple and complex constructions. Furthermore, the apparatuses and methods provided by the invention exploit novel ways to form particle bridges that may serve as a frit structure in a microconduit through the use of particles having a smaller diameter than the diameter of the microconduit.

SUMMARY OF THE INVENTION

Accordingly, it is an object of the present invention to overcome the above-mentioned disadvantages of the prior art by providing improved methods and apparatuses for controlling the introduction and the packing of particles into microdevices.

Additional objects, advantages and novel features of the invention will be set forth in part in the description that follows, and in part will become apparent to those skilled in the art upon examination of the following, or may be learned by through routine experimentation during the practice of the invention.

In a first embodiment, the invention provides an apparatus for introducing particles into a microdevice conduit. The apparatus includes a microdevice and a dispenser. The microdevice includes a substrate having a microchannel formed therein and a cover plate arranged over the substrate such that the cover plate in combination with the microchannel at least partially defines the conduit. The conduit extends from an inlet to an outlet, and the inlet terminates at an opening located on an exterior surface of the microdevice. A slurry comprised of a plurality of particles, e.g., chromatographic separation beads, in a carrier fluid is contained in the dispenser. The dispenser has a dispensing orifice sized to allow flow of slurry therethrough without clogging. Also included is a means for positioning the dispensing orifice and the inlet in fluid-tight alignment with each other without extending the dispenser past the opening of the inlet. Fluid tight alignment of the dispensing orifice and the inlet allows a means for means for applying pressure, typically of greater than 1 atmosphere, to the slurry in the dispenser to transport the slurry into the conduit via the dispensing orifice and the inlet.

The inlet may extend through either one of the cover plate or the substrate, and the exterior microdevice surface on which the inlet opening is located may be substantially planar. In addition, the positioning means may be comprised of a means for moving the dispenser and a means for immobilizing the microdevice. Furthermore, a seating member may be provided through which fluid communication is provided between the dispensing orifice and the inlet.

Optionally, a means is provided for filling the dispenser with fluid or slurry. The filling means may be constructed to fill the dispenser through the dispensing orifice. In addition or in the alternative, the filling means may be constructed to fill the dispenser from a plurality of different fluid or slurry sources.

In another embodiment, the invention provides a method for introducing particles into a microdevice conduit. The method involves the use of a microdevice and a dispenser as described above. The dispensing orifice of the dispenser and the inlet of the microdevice are positioned in fluid-tight alignment with each other in a manner such that the dispenser does not extend past the opening of the inlet. Then, pressure is applied to the slurry in the dispenser. As a result, slurry is transported into the conduit via slurry flow through the dispensing orifice and the inlet. Optionally, the slurry is agitated before its introduction into the microdevice.

In some instances, the inventive method may be carried out to transport a plurality of different slurries, or a combination of fluids and slurries, through the inlet into the conduit. In such case, each slurry typically contains particles of different sizes and functionalities. In addition, when slurries are successively transported through the dispenser, residue from each slurry may be removed from the dispenser before the subsequent slurry is loaded into the dispenser.

In still another embodiment, the invention provides a microdevice as described above, containing a plurality of particles each individually sized to travel through the inlet and the conduit. In some instances, the particles occupy at least about 25 volume percent of the conduit. In addition or in the alternative, the conduit may extend from an inlet through a bridging zone toward an outlet. The particles may form a particle bridge in the bridging zone. The particles may be introduced into the microdevice using the inventive method.

BRIEF DESCRIPTION OF THE DRAWINGS

FIG. 1A illustrates a microdevice in an open form. FIG. 1B depicts the microdevice in a closed form. FIG. 1C depicts the microdevice in schematic cross sectional view. FIG. 1D-1G depicts a dispenser in the form of a storage tube being loaded. FIG. 1H depicts the loading of microdevice by placing the storage tube in direct contact with the microdevice. FIG. 1I depicts the loading of microdevice by placing the storage tube in contact with the microdevice via an intermediate seating member.

FIG. 3A depicts the loading of the chromatographic column with particles of a relatively small diameter. FIG. 3B depicts the loading of the chromatographic column with particles of a relatively large diameter.

DETAILED DESCRIPTION OF THE INVENTION

Figure 1A:
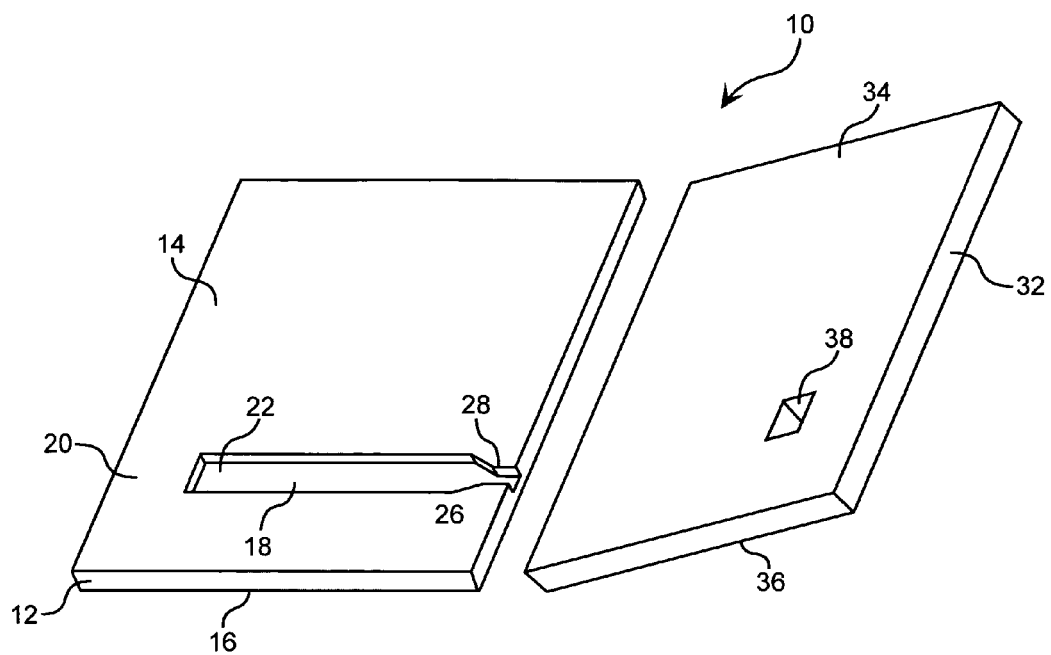
FIGS. 1A–1I, collectively referred to as FIG. 1, schematically depict an exemplary method of the invention that is carried out by an exemplary apparatus of the invention.

Before the invention is described in detail, it is to be understood that unless otherwise indicated this invention is not limited to particular materials, components or manufacturing processes, as such may vary.

It is also to be understood that the terminology used herein is for purposes of describing particular embodiments only, and is not intended to be limiting. It must be noted that, as used in the specification and the appended claims, the singular forms "a," "an" and "the" include plural referents unless the context clearly dictates otherwise. Thus, for example, reference to "a dispensing orifice" includes a single dispensing orifice as well as a plurality of dispensing orifices, reference to "a conduit" includes one or more conduits, and the like.

In this specification and in the claims which follow, reference will be made to a number of terms which shall be defined to have the following meanings:

The term "conduit" as used herein refers to a three-dimensional enclosure through which fluid may be transported, and is formed by one or more walls and that extends from a first terminal opening to a second terminal opening. The term "channel" is used herein to refer to an open groove or a trench in a surface. A channel in combination with a solid piece over the channel may form a conduit. Conduits and channels are "fluid-transporting features," i.e., an arrangement of solid bodies or portions thereof that direct fluid flow. Fluid-transporting features include, but are not limited to, chambers, reservoirs, inlets, outlets, conduits, and channels.

The term "fluid" as used herein refers to matter that is nonsolid, or at least partially gaseous and/or liquid. A fluid may contain a solid that is minimally, partially, or fully solvated, dispersed, or suspended. For example, a "slurry" is a type of fluid comprised of particles dispersed or suspended in a liquid carrier.

The term "fluid-tight" is used herein to describe the spatial relationship between two solid items having surfaces in direct or indirect physical contact such that fluid is prevented from flowing between an interface between the item surfaces.

The term "in order" is used herein to refer to a sequence of events. When a fluid travels "in order" through an inlet and a conduit, the fluid travels through the inlet before traveling through the conduit. "In order" does not necessarily mean consecutively. For example, a fluid traveling in order through an inlet and outlet does not preclude the fluid from traveling through a conduit after traveling through the inlet and before traveling through the outlet.

The prefix "micro" as used in the term "microdevice" refers to a device having features of micron or submicron dimensions, and which can be used in any number of chemical processes or fluid transport techniques involving very small amounts of fluid. Such processes and techniques include, but are not limited to, electrophoresis (e.g., CE or MCE), chromatography (e.g., μLC), screening and diagnostics (using, e.g., hybridization or other binding means), and chemical and biochemical synthesis (e.g., DNA amplification as may be conducted using the polymerase chain reaction, or "PCR"). The features of the microdevices are adapted to the particular use. For example, microdevices may contain a microconduit on the order of 1 μm to 200 μm in diameter, typically 5 μm to 75 μm, when the cross sectional shape of the microconduit is circular, and approximately 1 mm to 100 cm in length. Other cross-sectional shapes, e.g., rectangular, square, triangular, pentagonal, hexagonal, etc., having dimensions similar to above may be employed as well. In any case, such a microconduit may have a volume of about 1 pl to about 100 μl, typically about 1 nl to about 20 μl, more typically about 10 nl to about 1 μl. Other uses of the prefix have an analogous meaning.

"Optional" or "optionally" as used herein means that the subsequently described feature or structure may or may not be present, or that the subsequently described event or circumstance may or may not occur, and that the description includes instances where a particular feature or structure is present and instances where the feature or structure is absent, or instances where the event or circumstance occurs and instances where it does not. Mere reference to a feature, structure, event or circumstance as "optional," does not imply in any way whether the feature, structure, event or circumstance is be preferred.

The term "substantially" as in "substantially identical in size" is used herein to refer to items that have the same or nearly the same dimensions such that corresponding dimensions of the items do not differ by more than approximately 15%. Preferably, the corresponding dimensions do not differ by more than 5% and optimally by not more than approximately 1%. For example, particles that are substantially identical in size have diameters that do not differ from each other by more than approximately 15%. Other uses of the term "substantially" have an analogous meaning.

The term "constructed" as used herein refers to forming, assembling, modifying or combining components to build at least a portion of the inventive microdevice. Thus, "a conduit constructed for separating" as used herein refers to assembling or combining parts to form a conduit or modifying a surface of a conduit, wherein the conduit serves to differentiate or discriminate sample fluid components. For example, a conduit constructed for separating the components of a fluid sample may have a chemically, mechanically or energetically modified interior surface that interacts with different components differently, or may contain separating media such as chromatographic packing material.

In general, the invention relates to apparatuses and methods for introducing particles such as chromatographic separation beads into a conduit of a microdevice. Pressure is applied to a slurry of particles in a manner effective to induce slurry flow through a dispensing orifice of a dispenser and an inlet of the microdevice. As result, the conduit is packed with particles. Typically, the invention results in a packing density of at least about 25 volume percent of the conduit. In addition, the microdevice may be constructed such that the conduit exhibits a shape effective to control and/or eliminate formation of particle bridges therein. The invention is particularly suited for use with standardized automatic fluid handling and loading equipment.

The invention provides a number of novel features that address a number of needs pertaining to the introduction of particles in to a conduit of a microdevice. First, the invention allows for metered injection of a specific amount of slurry into the microdevice through the rapid formation of a seal capable of withstanding the pressures necessary to carry out such metered injection. As a result, multiple types of media suspensions may be rapidly injected in succession or in parallel into a single device. In contrast to technologies that exhibit problems associated with particle bridge formation, the invention exploits the particle packing phenomenon. Through the use of geometries to effect changes in fluid velocity, particle bridges are formed which serve as frits.

FIG. 1 depicts an exemplary method of the invention that is carried out by an exemplary apparatus of the invention. As is the case with all figure referenced herein, in which like parts are reference by like numerals, FIG. 1 is not to scale, and certain dimensions may be exaggerated for clarity of presentation. As illustrated in FIG. 1, a microdevice 10 is provided for loading. As depicted, the microdevice 10 is formed from a substrate 12 and a cover plate 32. FIG. 1A illustrates the microdevice 10 in an open form. The substrate 12 generally comprises first and second substantially planar opposing surfaces indicated at 14 and 16, respectively. The substrate 12 has a microchannel 18 in the first planar surface 14. The microchannel has an upstream region 20 that terminates at an inlet terminus 22 and a downstream region 24 that terminates at terminus 26 located at a protruding edge of the substrate surface 14. It will be readily appreciated that although the microchannel 18 has been represented in a generally extended form having a uniform width (and cross-sectional area) along its length, a neck region 28 having a narrower width (and smaller cross-sectional area) is depicted. As discussed below, such a neck region can be employed to facilitate particle trapping.

In general, microchannels can have a variety of configurations, such as in a straight, serpentine, spiral, or any tortuous path desired. Further, the microchannel 18, while depicted as having a rectangular or square cross-section, can be formed in a variety of channel cross-section geometries including semi-circular, rectangular, rhomboid, and the like, and the channels can be formed in a wide range of aspect ratios. It is also noted that a device having a plurality of microchannels thereon falls within the spirit of the invention. Optionally, the first planar surface 14 of the substrate may include other features such as cavities, orifices, additional microchannels and the like depending on the desired function(s) of the microdevice. Such features may be formed in any geometry and with any aspect ratio, limited only by the overall thickness of the substrate. In addition, features such as inlets and outlet may be formed on, in, or through lateral, top, and/or bottom surfaces.

The cover plate 32 is provided having opposing surfaces 34 and 36, wherein surface 34 is substantially planar and capable of interfacing in a fluid-tight manner with the first planar surface 14 of the substrate 12. An inlet 38 is depicted extending through surfaces 34 and 36. However, the inlet may be formed in the substrate, by a particular arrangement substrate and cover plate features as well. As is the case with the substrate surface 14, surface 34 of the cover plate 32 may include other features such as cavities, orifices, microchannels.

As shown in FIG. 1A, the cover plate 32 may be formed from a discrete component separate from the substrate 12. In general, a discrete cover plate may require microalignment means align the cover plate with the substrate to ensure precise microalignment of microfabricated features in a microdevice. Microalignment means can be formed either by laser ablation or by other methods of fabricating shaped pieces well known in the art. Representative microalignment means that can be employed herein include a plurality of co-axially arranged apertures microfabricated in component parts and/or a plurality of corresponding features substrates, e.g., projections and mating depressions, grooves and mating ridges or the like. Alternative alignment means includes, but are not limited to, features forms in component parts such as pin and mating apertures.

Alternatively, the substrate and the cover plate may be formed in a single, solid flexible piece, e.g., as described in U.S. Pat. No. 5,792,943 to Craig (not shown). In such a case, the flexible substrate may include first and second portions, corresponding to the substrate and the cover plate, wherein each portion has a substantially planar interior surface. The first and second portions may be separated by at least one fold means, such that the portions can be readily folded to overlie each other. The fold means can comprise a row of spaced-apart perforations ablated in the flexible substrate, a row of spaced-apart slot-like depressions or apertures ablated so as to extend only part way through the flexible substrate, or the like. The perforations or depressions can have circular, diamond, hexagonal or other shapes that promote hinge formation along a predetermined straight line. The fold means may also serve to align the cover plate with the substrate.

Like the substrate, the cover plate of the above described device can also include a variety of features such as apertures, microchannels, cavities, which have been formed therein (not shown). For example, when one wishes to form a conduit having a circular cross-section, mating microchannels each having a semicircular cross-sectional area may be formed on the contact surfaces of the cover plate and the substrate. Such mating microchannels, in combination with each other may form a conduit having a circular cross-section.

The materials used to form the substrate and cover plate in the microdevice of the invention as described above are selected with regard to physical and chemical characteristics that are desirable for sample handling and electrospray. In all cases, the substrate must be fabricated from a material that enables formation of high definition (or high "resolution") features, i.e., microchannels, chambers and the like, that are of micron or submicron dimensions. That is, the material must be capable of microfabrication using, e.g., dry etching, wet etching, laser etching, molding, embossing, or the like, so as to have desired miniaturized surface features; preferably, the substrate is capable of being microfabricated in such a manner as to form features in, on and/or through the surface of the substrate. Microstructures can also be formed on the surface of a substrate by adding material thereto. For example, polymer channels can be formed on the surface of a substrate using photo-imageable polyimide. Also, all device materials used should be substantially chemically inert and physically stable with respect to any substance with which they come into contact (e.g., with respect to pH, electric fields, etc.). For example, microdevices suitable for use with biochemical analysis should be biofouling resistant.

Typically, the substrate and/or cover plate are comprised of an electrically insulating material. Polymeric materials are particularly preferred herein, and will typically be organic polymers that are homopolymers or copolymers, naturally occurring or synthetic, crosslinked or uncrosslinked. Specific polymers of interest include, but are not limited to, polyimides, polyketones, polysulfones, polycarbonates, polyesters, polyamides, polyethers, polyurethanes, polyfluorocarbons, polystyrenes, polyacrylonitrile, polybutadiene, polystyrene, acrylate and acrylic acid polymers such as polymethyl methacrylate, silicones, substituted and unsubstituted polyolefins, and copolymers thereof. Polyimides and polyketones are of particular interest due to their resistance to biofouling and are a highly desirable substrate material in a number of contexts. Polyimides are commercially available, e.g., under the tradename Kapton®, (DuPont, Wilmington, Del.) and Upilex® (Ube Industries, Ltd., Japan). In addition, polyetheretherketone (PEEK) has been found to exhibit excellent resistance to biofouling and is therefore a preferred polyketone. However, other electrically insulating materials may be used as well. For example, ceramics (including aluminum oxide and the like) and glasses (silicates, borosilicates, and the like) are generally considered electrically insulating. In addition, or in the alternative, the substrate and/or cover plate may be comprised of an electrically conductive material. For example, any of a number of metals or carbonaceous materials may be used to form a conductive cover plate and/or the substrate.

The substrates and cover plates of the invention may also be fabricated from a composite, i.e., a composition comprised of unlike materials. The composite may be a block composite, e.g., an A-B-A block composite, an A-B-C block composite, or the like. Alternatively, the composite may be a heterogeneous combination of materials, i.e., in which the materials are distinct from separate phases, or a homogeneous combination of unlike materials. As used herein, the term "composite" is used to include a "laminate" composite. A "laminate" refers to a composite material formed from several different bonded layers of identical or different materials. Other preferred composite substrates include polymer laminates, polymer-metal laminates, e.g., polymer coated with copper, a ceramic-in-metal or a polymer-in-metal composite. One preferred composite material is a polyimide laminate formed from a first layer of polyimide such as Kapton®, available from DuPont (Wilmington, Del.), that has been co-extruded with a second, thin layer of a thermal adhesive form of polyimide known as KJ®, also available from DuPont (Wilmington, Del.).

The features of the microdevice, e.g., fluid-transporting features, microalignment features, etc., may be formed using any method suitable for microdevice fabrication, including, but not limited to, micromolding and casting techniques, embossing methods, surface micro-machining and bulk-micromachining. The latter technique involves formation of microstructures by etching directly into a bulk material, typically using wet chemical etching or reactive ion etching ("RIE"). Surface micro-machining involves fabrication from films deposited on the surface of a substrate. An exemplary surface micro-machining process is known as "LIGA." See, e.g., Becker et al. (1986), "Fabrication of Microstructures with High Aspect Ratios and Great Structural Heights by Synchrotron Radiation Lithography Galvanoforming, and Plastic Moulding (LIGA Process)," *Microelectronic Engineering* 4(1):35–36; Ehrfeld et al. (1988), "1988 LIGA Process: Sensor Construction Techniques via X-Ray Lithography," *Tech. Digest from IEEE Solid-State Sensor and Actuator Workshop*, Hilton Head, S.C.; Guckel et al. (1991) *J. Micromech. Microeng.* 1: 135–138.

Figure 1B:
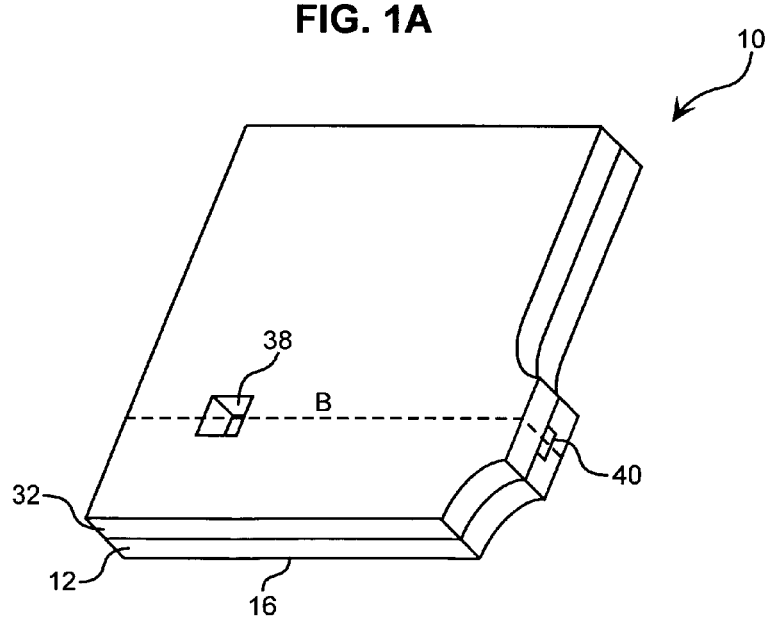

As shown in FIG. 1B, the cover plate 32 is arranged over substrate surface 14. The cover plate surface 34 is placed over surface 14 such that fluid-tight contact is achieved between surfaces 14 and 34. Fluid-tight contact may be achieved using pressure sealing techniques, by using external means to urge the pieces together (such as clips, tension springs or other clamping apparatus), or by using adhesives.

It should be noted that the invention is not limited to two-layer devices such that the microdevice depicted in FIG. 1. For example, a microdevice having the same conduit arrangement as that depicted in FIG. 1, may be formed from three (or more) layers. This may be achieved by interposing a middle layer containing a channel-shaped cutout between two substantially planar cover plates. It should be further evident that additional layers in the form of substrates and/or cover plates may be included to form a multilayered network of conduits for conveying fluid.

Figure 1C:
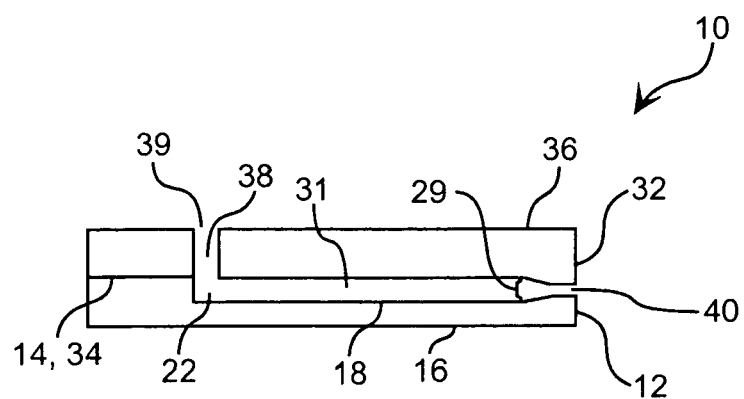
Figures 1D, 1E, 1F, 1G:
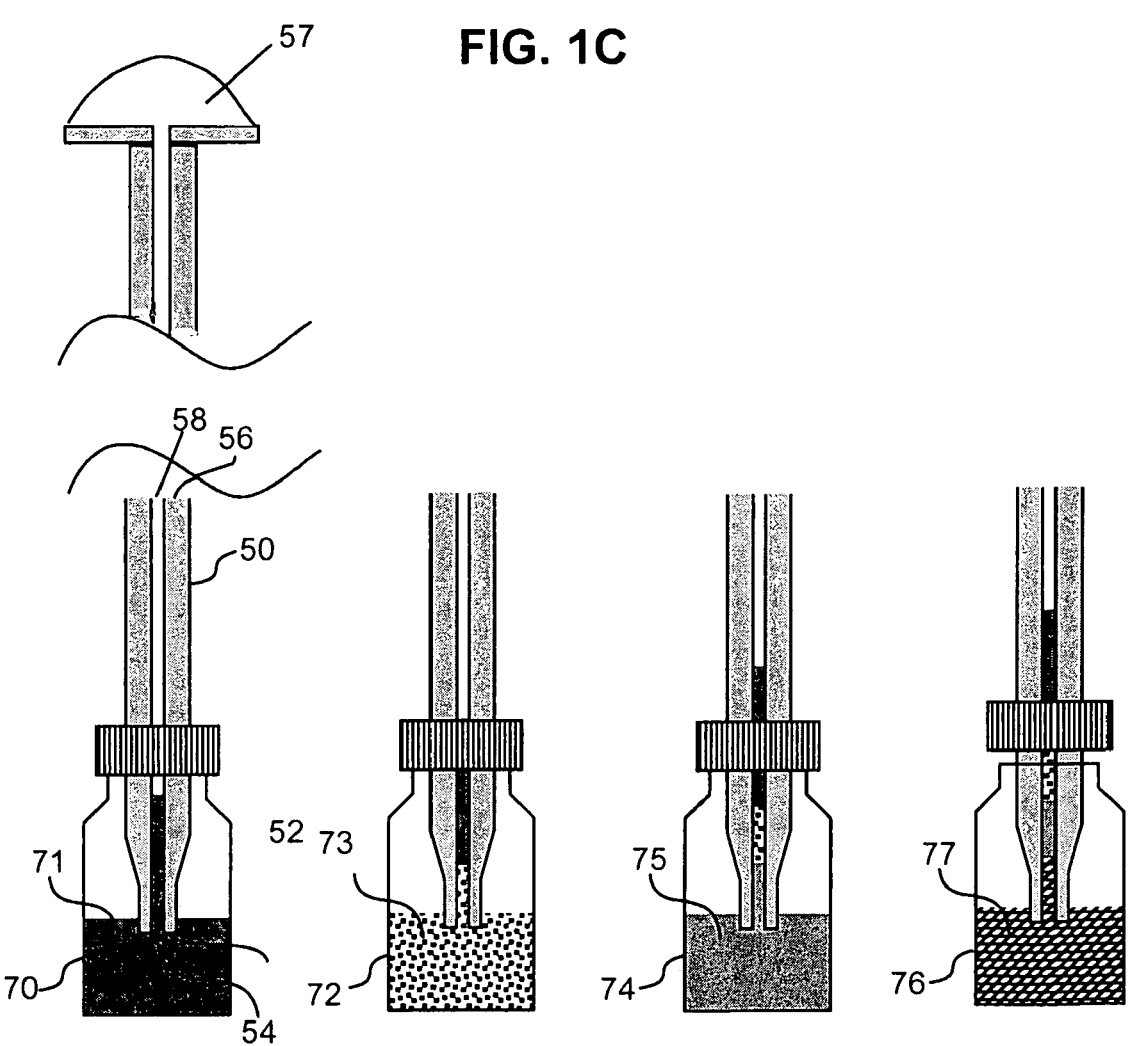

As illustrated in schematic cross sectional view, FIG. 1C depicts an arrangement of cover plate 32 over the substrate surface 14 results in the formation of microconduit 31. Microconduit 31 is defined by the microchannel 18 in combination and the cover plate contact surface 34. Thus, while the upstream region of the microconduit 31 may generally exhibit a uniform cross-sectional area, the constriction region 29 of the microconduit, which corresponds to the neck 28 region of the microchannel, may exhibit a smaller cross-sectional area.

Inlet 38 is aligned with the inlet terminus 22. Since inlet 38 extends through surface 36, an inlet opening 39 is formed on an exterior surface 36 of the microdevice. Once assembled, a flow path is formed in the device that travels, in order, through inlet 38, microconduit 31, constriction region 29, and outlet 40.

It should be noted that any of the above feature-forming techniques may also be used to provide for features of sufficiently high definition, i.e., microscale components, channels, chambers, etc., such that microalignment of these features is possible. Optionally, material may be removed from the cover plate and/or substrate to form an exterior microdevice surface and to form an expose a downstream portion of an emitter that protrudes from the exterior surface. Techniques for carrying out such material removal are described in U.S. patent application Ser. No. 09/711,804 ("A Microdevice Having an Integrated Protruding Electrospray Emitter and a Method for Producing the Microdevice"), inventors Brennen, Yin and Killeen, filed on Nov. 13, 2000. Alternative or additional functionalities such as an integrated detection means, reaction chambers, particle-packed reaction beds, and such, may be included as well.

The inventive apparatus also includes a dispenser. Any of a number of different dispensers may be used as long as the dispenser has a dispensing orifice through which a fluid and/or slurry may flow. Exemplary dispensers may be formed from capillaries, needles, pipettes, transfer lines, or combinations thereof. As depicted in FIG. 1D-1I, a dispenser is provided in the forma of a storage tube 50 having two termini. Located at a first terminus 52 is a dispensing orifice 54. A pressure applying means is provided to communicate with the second terminus 56 of the dispenser. For example, the pressure applying means may be a plunger 57 (schematically shown in FIG. 1D) that slidably located within the storage tube and forms a fluid-tight seal against the lumen wall of the tube. In such an instance, the plunger 57 may also serve as a means for filling the dispenser. That is, the plunger 57 may be used to draw fluid into or expel fluid out of the storage tube via the dispensing orifice. However, other pressure applying means and/or filling means, e.g., mechanical, diffusion, vacuum, or other type of pumps, may be used as well.

The dispenser may be used to introduce one or more fluids and/or slurries in series into the microconduit. When a plurality of fluids is to be introduced into the microconduit, they typically differ in composition from one another. Similarly, when a plurality of slurries is used, the composition of the slurries may differ. In particular, the particles in the slurries may have different functionalities. For example, as depicted in FIGS. 1D–1G, provided are containers, indicated at 70, 72, 74, and 76, holding a small-particle slurry 71, a separation fluid 73, a large-particle slurry 75, and a column-preparation fluid 77, respectively. As depicted, the first terminus 52 of the storage tube 50 is submerged in the small-particle slurry 71, and a filling means provides a motive force to draw a desired amount of the small particle slurry through the dispensing orifice 54 and into the storage tube 50. Similarly, the separation fluid 73, the large-particle slurry 75, and the column preparation fluid 77 are drawn into the tube 50. As a result, the storage tube is loaded along its length starting from the first terminus 52, the column-preparation fluid 77, the large-particle slurry 75, the separation fluid 73, and the small-particle slurry 71. Alternatively, slurries may be loaded through the opening 56 at the second terminus 54 of the storage tube 50 (not shown). Once filled, the storage tube 50 is ready for use in loading the microconduit 31.

The invention allows variations in dispenser construction. In some embodiments, relative motion is provided between the means for filling the dispenser and the dispenser. Such relative motion may be effected by moving the filling means and/or the dispenser. In addition, a plurality of dispensers may be included each having a dispensing orifice. In such a case, each dispenser may contain a different fluid or slurry. A positioning means may be constructed to position the dispensing orifices successively in fluid-tight alignment with the inlet.

Figure 1H:
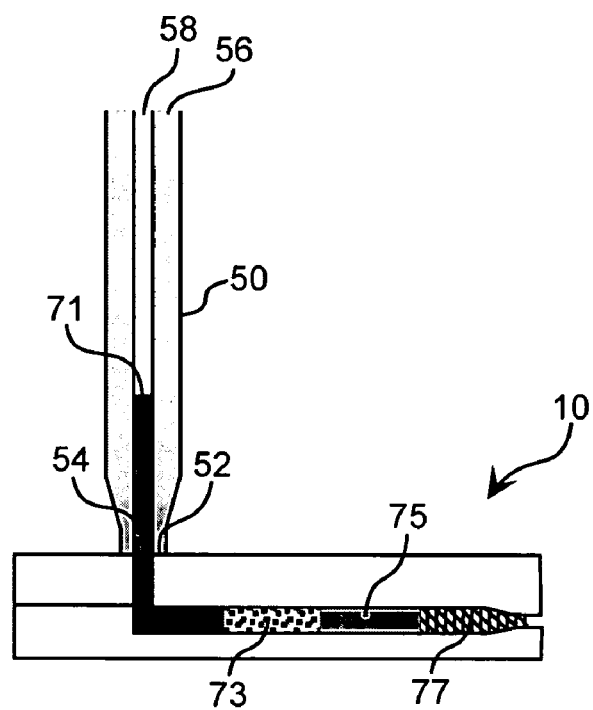

In any case, the dispensing orifice 54 (or orifices) and the inlet 38 are placed in fluid-tight alignment without extending the dispenser past the opening 39 of the inlet that lies on the exterior surface 36 of the microdevice 10. In some instances, as illustrated in FIG. 1H, the microdevice 10 may be immobilized on a stage, and the first terminus 52 of the storage tube 50 is placed in direct contact and fluid tight alignment with the inlet 38 of the microdevice 10. When a needle is used as the storage tube, the small area of contact between the needle tip and the microdevice may result in a high local pressure seal which can withstand hundreds of bars of fluidic pressure. Such a configuration is particularly useful in instances where successful packing requires high pressures. For example, the inventive apparatus may involve the use of a pressure-applying means capable of applying a pressure greater than about 10 bars to the slurry within the dispenser. In some instances, a pressure greater than about 50 bars may be applied to the slurry within the dispenser.

Figure 1I:
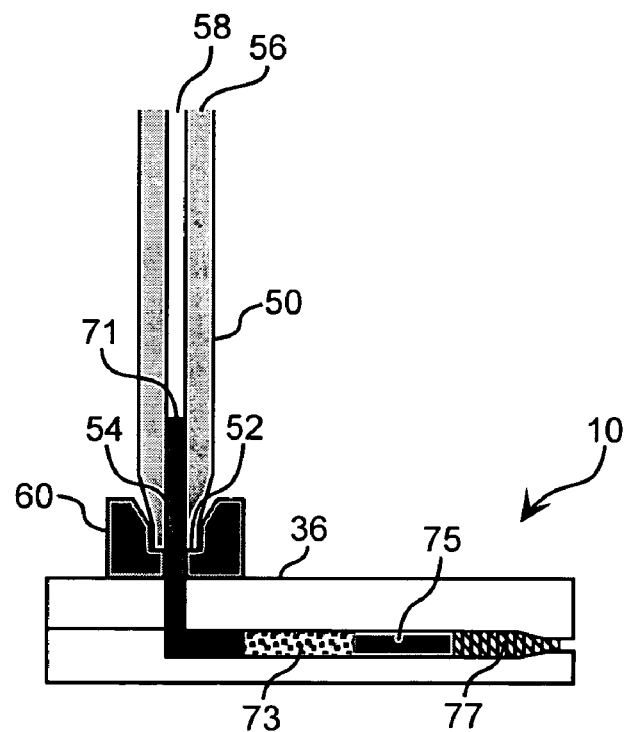

Alternatively, an intermediate seating member 60 may be used between the dispenser 50 and the microdevice 10 to be packed. Such intermediate seating members may serve a number of functions, including, but not limited to, seating and/or sealing the dispenser against an exterior surface of the microdevice and providing an alignment means between the dispenser terminus 52 and the microdevice inlet 38. FIG. 1I depicts a seating member 60 between the storage tube 50 and the inlet 38. The seating member 60 forms a tight seal against an exterior surface of the tube 50 and against an exterior surface 36 of the microdevice 10.

The intermediate seating member may be formed from any number of materials depending on the construction of the microdevice and the dispenser. Typically, a polymeric material is used. The seating member may, in the alternative or in addition, be a ceramic, a metal, a glass, or a combination thereof as well.

The shape and mechanical properties of the intermediate seating member are dictated at least in part by the shape and mechanical properties of the microdevice and the dispenser. For example, when both the microdevice and the dispenser are made from rigid materials, the seating member may be formed from a deformable material that is compliant relative to both the microdevice and the dispenser. When the seating member is constructed for reuse, an elastically deformable material is preferred over a plastically deformable material. In addition, a deformable material is particularly useful when either or both the microdevice has a nonplanar exterior surface against which the seating member forms a seal. For example, a specially-designed seating member comprising an elastically deformable polymeric material may serve as an interface between a dispenser, e.g., a needle in fluid communication with a reservoir, and a standard capillary chromatography column or nano-column fitting. Such a seating member may eliminate any need for screw fitting ordinarily associated with chromatographic columns.

As alluded to above, a positioning means may be used to provide fluid communication between the dispensing orifice and the inlet through the seating member. The positioning means may be constructed, for example, from mechanical, electrical, or pneumatic means as well as motors, levers, pulleys, gears, or a combination thereof. In some instances, robotic positioning means known to those of ordinary skill in the art may be used to align the dispensing orifice with the inlet. Although either or both the dispenser and the microdevice may be moved, the positioning means typically includes a means for moving the dispenser. Such a moving means may serve to move the dispenser along or rotate the dispenser about a single axis, e.g., a vertical axis. In addition, such moving means may be used in combination with a means for immobilizing the microdevice.

Typically, no portion of the storage tube 50 extends past inlet opening 39. Once fluid tight alignment is achieved, pressure is applied to the fluids and slurries within the storage tube. As a result, the fluids and slurries within the storage tube 50 are driven through the dispensing orifice 54 and into the inlet 38 of the microdevice 10. That is, the column-preparation fluid, the large-particle slurry, the separation fluid, and the small-particle slurry are successively loaded into the microconduit 31. As depicted in FIGS. 1H and 1I, the large particles of the large-particle slurry, under pressure by a motive force means, travel the length of the microconduit 31 until they reach the constriction region 29. Often, the same motive force means used to load the dispenser may be used to unload the dispenser as well. Due to the relative size of the large particles and the diameter of the constriction region, the particles are trapped within the conduit at the constriction region. Similarly, the small particles of the small-particle slurry travel the length of the microconduit 31 until they impinge on the large particles trapped at the constriction region 29. In short, the large particles form a loose frit structure for the smaller particles. Once loaded, the microconduit is ready for use. Of course, a single fluid or a single slurry may be loaded as well.

In some embodiments, the invention provides a method that takes advantage of the phenomenon that large particles generally settle in a liquid faster than smaller particles of the same density. In this technique, a single slurry containing both large and small particles may be loaded into a storage tube that is positioned vertically. After a period of time, the larger particles settle to the bottom faster than the smaller particles. As a result, there is a predominance of larger particles at the bottom. Thus, a parallel loading technique for slurries of differently-sized particle may be converted effectively into a serial loading technique.

For either of the above-techniques, the fluid velocity profile of the slurry through a cylindrical storage tube is parabolic. This may occur while the tube is located or discharged. Because fluid at the center of the tube will tend to flow faster than fluid near the tube wall, there is a possibility that a preceding slurry will not have fully exited the tube before the subsequent slurry starts exiting the column. Avoiding such "out-of-turn" slurry flow, may involve loading a sufficiently low volume of the last slurry in the tube such that the last slurry is completely expelled from the tube before the penultimate slurry begins to emerge from the tube. In addition, an intermediate fluid "buffer," e.g., as depicted in FIG. 1, can be introduced into the tube between each successive slurry such that one slurry fully exits the tube prior to the beginning of the exit of the next slurry.

Any of a number of known liquid chromatographic packing materials may be included in the sample conduit. Such packing materials typically exhibit a surface area of about 100 to about 500 $m^2/g$ to achieve high separation efficiency and capacity. Accordingly, packing materials containing particles of different porosities may be advantageously used. In addition, packing materials may have surfaces that are modified for the intended separation of given classes of samples. For example, particles having different functionalities, e.g., different enzymes attached to beads, media having different chemical affinities, etc., may be used to separate and/or process samples that contain biomolecules such as nucleotidic and/or peptidic moieties. Furthermore, separation beads may be adapted to separate fluid sample components according to properties such molecular weight, polarity, hydrophobicity or charge.

It should be noted that other aspects of known separation technology may be incorporated in the practice of the present invention. For example, in typical liquid chromatographic columns, some means is typically used retain chromatographic separation beads and to prevent small diameter beads from washing entirely through the column when a fluid sample and/or a mobile phase is conveyed through the column. Typically, such retaining means include a frit structure. Frit structures may vary in construction according to their application. In larger diameter columns, for example, a separately formed structure may be immobilized downstream from the beads. In smaller diameter columns, such as those in capillary liquid chromatography columns, the frit can be formed in place by immobilizing the particles in a specific place. In some instances, frits are used both upstream and downstream from the particles to maintain the particles in place.

Similarly, when ordinary liquid chromatography packing material is slurry-packed within a separation conduit of a microdevice, a frit structure, micromachined or otherwise, may be included near or at the sample outlet. It should be noted, however, that frit structures in the context of microfluidic or chip-based devices pose a number of technical challenges. In general, it can be difficult to place or maintain an external frit in position relative to the microdevice. In addition, it can also be difficult to form certain types of frit structures via ordinary micromachining techniques. Thus, frits made from particulates and/or fibers may be placed downstream from a chromatographic packing material in the separation conduit a microdevice. For example, sintered beads or a metal fiber mesh forming frit having an average pore size of 2.0 µm may be placed downstream from a plurality of chromatographic beads having an average diameter of 3.5 µm. As alluded to above, the cross-sectional area of the separation conduit may be reduced downstream from the frit structure, particularly if the sample outlet is a part of an electrospray tip as described, for example, in U.S. Ser. No. 09/711,804.

Figure 2:
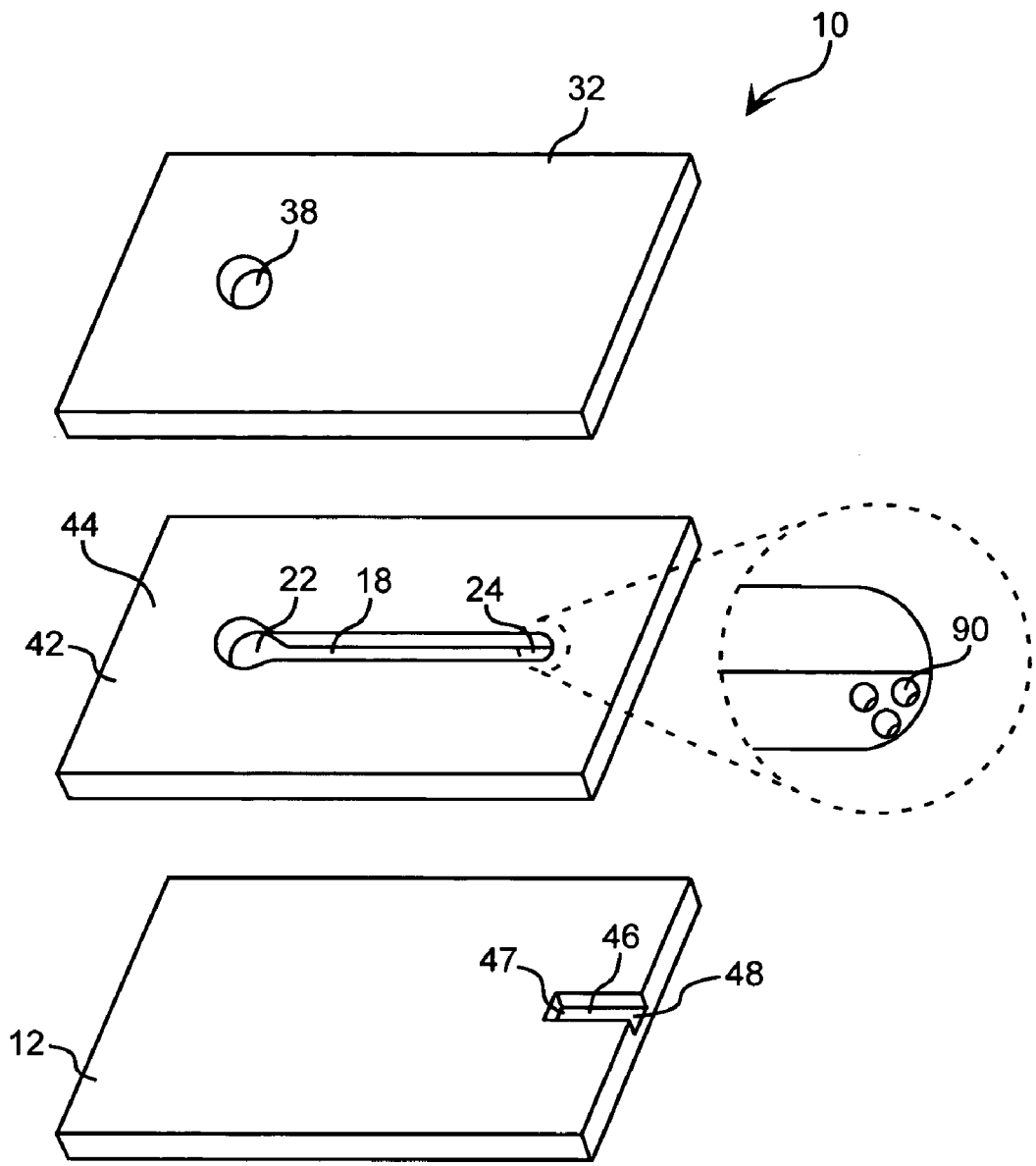
FIG. 2 schematically depicts a microdevice having a frit structure that is particularly suited for production via micromachining techniques.

FIG. 2 depicts a microdevice having a frit structure that is particularly suited for many micromachining techniques. The microdevice 10 is comprised of a cover plate 32, an intermediate layer 42, and a substrate 12. An inlet 38 extends through the cover plate 32. A separation microchannel 18 extending from an upstream terminus 22 to a downstream terminus 24 is located in the upper surface 44 of the intermediate layer 42. A frit structure 90 in the form of through-holes is located in the downstream terminus 24 of the microchannel 18. A substrate microchannel 46 extends from an upstream terminus 47 to a downstream edge 48 of the substrate. When assembled, the inlet 38 is aligned with the upstream terminus 22 of the separation microchannel 18, and the frit structure 90 is aligned with the upstream terminus 47 of the substrate microchannel 46. As a result, a conduit is formed having a flow path that extends, in order, through the inlet 38, the separation microchannel 18, the frit structure 90, and the substrate microchannel 46. Optionally, particles, e.g., separation media, may be placed within the separation channel. In such a case, the frit structure serves to maintain the particles in place by the frit structure when a sample or a mobile phase flows through conduit.

In general, packing performance represents an important aspect of the invention. Packing performance, in turn, depends on the techniques used to introduce fluid, slurries, and/or particles into the microdevice conduit. Accordingly, depending on the desired packing performance, certain techniques may be selectively used to achieve the desired packing performance. For example, it is often desirable to ensure that the packing density of separation particles in a conduit of a microdevice does not fall below a minimum level. In some instances, the minimum level is about 25 volume percent of the conduit. More specifically, the minimum level may be about 50 volume percent. To avoid excess gap volume, a slurry containing the separation particles may be agitated before its introduction into the conduit. In addition, as discussed above, a plurality of fluids, slurries, and/or particles may be introduced into the microdevice conduit in succession. In some instances, a successor fluid may be used to remove residue from a predecessor slurry. Alternatively, a successor slurry may be used to supplement particles introduced by a predecessor slurry by introduce additional particles.

Figure 3A:
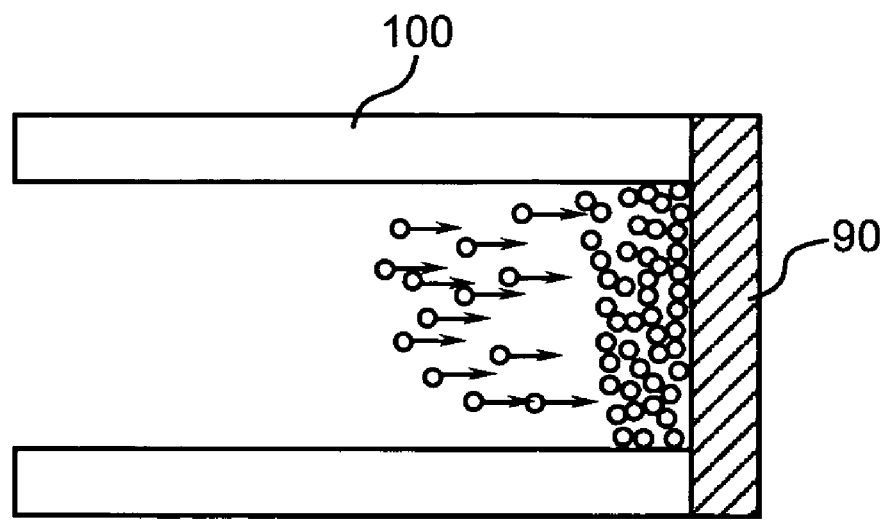
FIGS. 3A and 3B, collectively referred to as FIG. 3, schematically depict particle bridge formation in a chromatographic column.
Figure 3B:
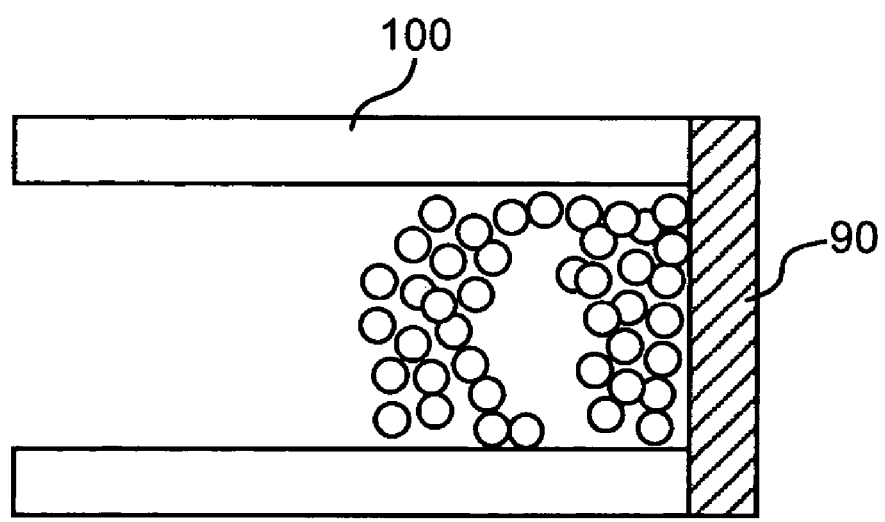

Particle bridge formation is a potential problematic phenomenon associated with the loading of chromatographic columns. Particle bridge build up during packing tends to lead to gaps with in the column and result in loss of separation efficiency. Particle bridge formation is depicted in FIG. 3. FIGS. 3A and 3B both depict in cross-sectional view the same chromatographic column 100. Downstream from the column is a frit structure 90. As depicted in FIG. 3A, when particles of a small diameter are introduced as a slurry into the column 100, a relatively high packing density may be achieved. However, as depicted in FIG. 3B, when particles of a larger diameter are introduced into the column 100, a particle bridge 110 may be formed at a bridging zone. In general, particle bridge formation should be avoided along the separation column because such formation lowers particle packing density. The likelihood of particle bridge formation typically increases when the column diameter to particle diameter ratio is 10 or less. This is supported by experimental observations showing that gaps can often form when 5 µm particles are packed into capillaries having a 50 µm internal diameter.

Figure 4:
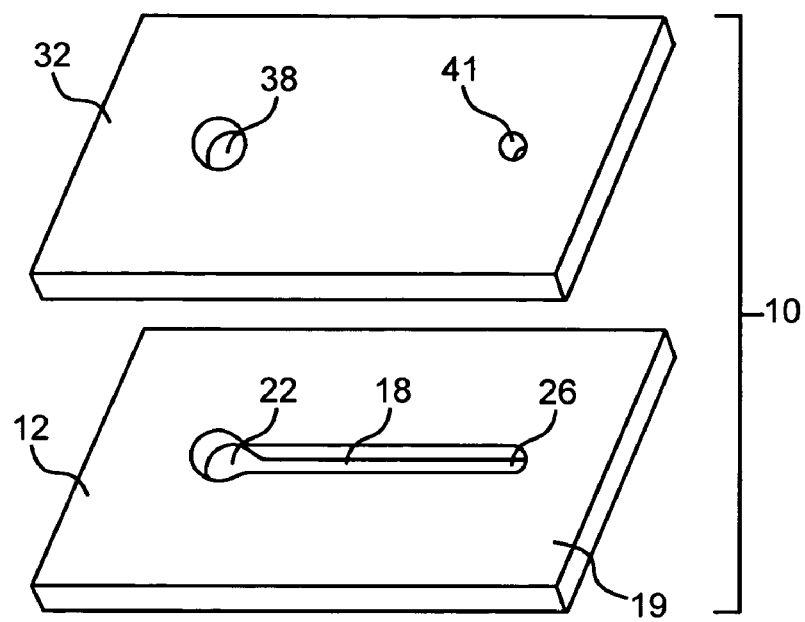
FIG. 4 schematically depicts an exemplary microdevice having a channel geometry having a low likelihood form particle bridge formation FIG. 5 schematically depicts exemplary microdevice geometries suitable for particle bridges formation at bridging zones.

Other factors such as the smoothness of the interior surface of the separation conduit and the rate of slurry flow also affect particle bridge formation. For example, smooth lumen surfaces, e.g., interior column surfaces, tend to inhibit particle bridge formation. FIG. 4 depicts an exemplary microdevice 10 having a channel geometry that has a low likelihood of particle bridge formation. The microdevice 10 is comprised of a substrate 12 having a microchannel 18 in surface 14 that narrows from an upstream terminus 22 to a downstream terminus 26. A cover plate 32 is arranged over the substrate 12 such that inlet 38 is aligned with upstream terminus 22 and outlet 41.

In addition, experimental observations indicate that bridges tend to build up more frequently at corners where fluid has to take a turn. Bridge formation has also been frequently observed when abrupt fluid transition occurs. That is, bridge formation tends to occur in regions that facilitate changes in fluid velocity.

Figure 5:
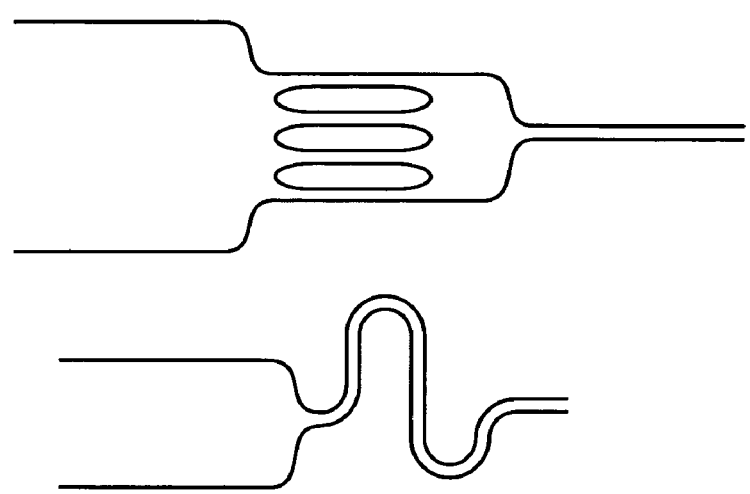

Thus, another embodiment of the invention exploits the particle bridge formation phenomenon to form frit structures. As discussed above, the likelihood of particle bridge formation typically increases when the column diameter to particle diameter ratio is 10 or less. It has been experimentally verified that particle bridge formation can be accurately and precisely controlled when the ratio of column diameter to particle diameter is 6 or less. Thus, a bridging zone may be formed in a column in a region having reduced diameter as compared to the rest of the column. For example, if an hour-glass shaped column is provided having a terminal diameter of at least 10 times the diameter of the particles to be introduced and a midsection diameter of less than 6 times the particle diameter, the midsection would represent a bridging zone. In addition, regions in columns that provide for a change in fluid flow velocity are particularly suited for particle bridge formation. FIG. 5 depicts exemplary channel geometries that may be employed so that particle bridges are formed at bridging zones, located where fluid flow changes speed and/or direction.

In short, the particle bridge formation can be exploited to allow particles to be retained within a microdevice conduit. Bridging zones are of particular interest because their inner cross-sectional area may be larger than the cross sectional area of individual particles. As a result, bridging zones and particles retained thereby, together or separately, can serve as a frit structure.

The microdevices may employ operation principles similar to those of ordinary liquid chromatography devices. Thus, there are instances in which ordinary liquid chromatography technology may be incorporated in the practice of the invention. For example, a fluid flow rate regulator for regulating flow rate may be employed to ensure that a mobile phase is delivered to the separation conduit at an appropriate rate and pressure. Such flow rate regulators may be interposed in the flow path between the mobile phase source and the integrated introducing means. The flow rate regulator may also include a flow splitter. Additionally, a flow sensor for determining and optionally controlling the rate of fluid flow into the sample inlet source may be provided.

In addition, the invention may be used in conjunction with other microfluidic technologies as well, for example, the invention may be used with a high-pressure pump is connected to a rotary valve. Such valves are described in U.S. Patent Application Publication No. 20030015682 to Killeen et al. In addition, it should be noted that an analyzer may be interfaced with any portion of the flow path of the inventive microdevice including in the inlet. The analyzer may be, for example, a mass spectrometer, in which case the outlet may be located within or adapted to deliver fluid sample to an ionization chamber. See U.S. Ser. No. 09/711,804. In addition, mass spectrometry technologies are well known in the art and may involve, for example, laser desorption and ionization technologies, whose use in conjunction with microdevices are described in U.S. Pat. Nos. 5,705,813 and 5,716,825.

In sum, the invention provides numerous advantages over packing methods and systems previously known in the art. For example, the invention provides a precise and automatable metering technique so as to control the amount of packing media introduced into the microdevice. The packing media can be loaded immediately before packing each device. In this way, the media slurry can be agitated and put into homogeneous suspension just before loading. This increases the repeatability of the amount of packing material loaded each time. In addition, no screw fittings are necessary to maintain an intact seal at high pressures, e.g., greater than 300 bar, between the dispenser and the microdevice. In addition, the invention provides a method for introducing a plurality of slurries in any desired order into the microdevice. Washing and/or other intermediate processes may be made in the reservoir between packings. For example, different affinity media may be loaded into microdevices with one or more washing steps to prevent carryover between the packing of each different media. Changes from one type of slurry to another type may be made rapidly and easily.

Variations on the present invention will be apparent to those of ordinary skill in the art. For example, because fluid flow control is an important aspect of the invention, fluid flow control means such as valves, motive force means, manifolds, and the like, may be used in conjunction with the invention. Such fluid flow control means may, for example, represent an integrated portion of the microdevices, modular units operably connectable with the microdevices, or a component of the dispenser. In addition, microdevices with additional functionalities, integrated or otherwise, may be used with the invention. For example, microdevices may be loaded with fluid samples for filtration, concentration, extraction, or other processing before delivery to an integrated electrospray emitter. Such variation may involve microdevices having multiple chambers, conduits, openings, inlets, outlets, etc While the invention has been described in conjunction with the preferred specific embodiments thereof, that the foregoing description is intended to illustrate and not limit the scope of the invention. Other aspects, advantages and modifications within the scope of the invention will be apparent to those skilled in the art to which the invention pertains.

All patents, patent applications, and publications mentioned herein are hereby incorporated by reference in their entireties.

We claim:

1. An apparatus for introducing particles into a microdevice conduit, comprising:
   a microdevice comprised of a substrate having a microchannel formed therein and a cover plate arranged over the substrate such that the cover plate in combination with the microchannel at least partially defines the conduit, wherein the conduit extends from an inlet to an outlet, and the inlet terminates at an opening located on an exterior surface of the microdevice;
   a dispenser containing fluid and having a dispensing orifice, wherein the dispensing orifice is sized to allow flow of the fluid therethrough without clogging;
   a means for positioning the dispensing orifice and the inlet in fluid-tight alignment with each other without extending the dispenser past the opening of the inlet; and
   a means for applying pressure to the fluid in the dispenser so as to transport the fluid into the conduit via the dispensing orifice and the inlet.

2. The apparatus of claim 1, wherein the microdevice is comprised of a plurality of substrates and/or cover plates.

3. The apparatus of claim 1, wherein the inlet extends through either the cover plate or the substrate.

4. The apparatus of claim 1, wherein the exterior microdevice surface on which the inlet opening is located is substantially planar.

5. The method of claim 1, wherein the fluid contains a slurry comprised of a plurality of particles in a carrier fluid.

6. The apparatus of claim 5, wherein the pressure-applying means is constructed to apply a pressure greater than about 1 bar to the slurry within the dispenser.

7. The apparatus of claim 6, wherein the pressure-applying means is constructed to apply a pressure greater than about 10 bars to the slurry within the dispenser.

8. The apparatus of claim 5, wherein the particles are chromatographic separation beads.

9. The apparatus of claim 1, wherein the positioning means is comprised of a means for moving the dispenser.

10. The apparatus of claim 9, wherein the moving means moves the dispenser along a vertical axis.

11. The apparatus of claim 9, wherein the moving means moves the dispenser along a single axis.

12. The apparatus of claim 9, wherein the moving means provides rotates the dispenser about a single axis.

13. The apparatus of claim 9, wherein the positioning means is further comprised of a means for immobilizing the microdevice.

14. The apparatus of claim 1, wherein the positioning means is comprised of a means for moving the microdevice.

15. The apparatus of claim 1, further comprising a seating member through which fluid communication is provided between the dispensing orifice and the inlet, when the dispensing orifice and the inlet are positioned in fluid-tight alignment.

16. The apparatus of claim 15, wherein the seating member is comprised of a polymeric material.

17. The apparatus of claim 15, wherein the seating member is comprised of a ceramic, a metal, a glass, or a combination thereof.

18. The apparatus of claim 1, further comprising a means for filling the dispenser with a fluid or a slurry.

19. The apparatus of claim 18, wherein the filling means is constructed to fill the dispenser through the dispensing orifice.

20. The apparatus of claim 18, wherein the filling means is constructed to fill the dispenser from a plurality of different fluid or slurry sources.

21. The apparatus of claim 18, further comprising a means for providing relative motion between the means for filling the dispenser and the dispenser.

22. The apparatus of claim 21, wherein the relative motion providing means moves the filling means.

23. The apparatus of claim 21, wherein the relative-motion providing means moves the dispenser.

24. The apparatus of claim 1, comprising a plurality of dispensers each having a dispensing orifice.

25. The apparatus of claim 24, wherein each dispenser contains a different fluid or slurry.

26. The apparatus of claim 24, wherein the positioning means is constructed to position the dispensing orifices successively in fluid-tight alignment with the inlet.

27. A method for introducing particles into a microdevice conduit, comprising:
（a) positioning
(i) a dispensing orifice of a dispenser and
(ii) an inlet of a microdevice that terminates at an opening located on an exterior surface of the microdevice in fluid-tight alignment with each other without extending the dispenser past the opening of the inlet, wherein the microdevice is comprised of a substrate having a microchannel formed therein and a cover plate arranged over the substrate such that the cover plate in combination with the microchannel at least partially defines the conduit, and the conduit extends from the inlet to an outlet, wherein the dispenser contains a fluid, and
the dispensing orifice is sized to allow flow of fluid therethrough without clogging; and
(b) applying pressure to the fluid in the dispenser so as to transport the fluid into the conduit via fluid flow through the dispensing orifice and the inlet.

28. The method of claim 27, wherein the fluid contains a slurry comprised of a plurality of particles in a carrier fluid.

29. The method of claim 28, further comprising, before step (a), (a') agitating the slurry.

30. The method of claim 27, further comprising, before step (b), (b') transporting a different fluid or slurry through the inlet.

31. The method of claim 30, wherein each slurry contains particles of a different functionality.

32. The method of claim 31, wherein each slurry contains particles associated with different enzymes.

33. The method of claim 30, wherein each slurry contains particles of a different porosity.

34. The method of claim 30, wherein each slurry contains particles of a different size.

35. The method of claim 27, further comprising, after step (b), (c) removing any residue of the slurry from the dispenser.

36. The method of claim 35, further comprising, after step (c), (d) repeating steps (a) and (b) to transport an additional fluid or slurry into the conduit through the dispensing orifice and the inlet.

37. The method of claim 36, wherein each slurry contains particles of a different functionality.

38. The method of claim 37, wherein each slurry contains particles associated with different enzymes.

39. The method of claim 36, wherein each slurry contains particles of a different porosity.

40. The method of claim 36, wherein each slurry contains particles of a different size.

41. The method of claim 27, wherein steps (a) and (b) are repeated for a different microdevice.

42. The method of claim 28, wherein the particles occupy at least about 25 volume percent of the conduit.

43. The method of claim 28, wherein a particle bridge is formed in a bridging zone within the conduit.

* * * * *